United States Patent
McCarthy et al.

(10) Patent No.: US 11,564,712 B2
(45) Date of Patent: Jan. 31, 2023

(54) CURVED CANNULA

(71) Applicants: Giovanna McCarthy, Liverpool, NY (US); Scott I. Gingold, Syracuse, NY (US)

(72) Inventors: Giovanna McCarthy, Liverpool, NY (US); Scott I. Gingold, Syracuse, NY (US)

(*) Notice: Subject to any disclaimer, the term of this patent is extended or adjusted under 35 U.S.C. 154(b) by 0 days.

(21) Appl. No.: 17/741,822

(22) Filed: May 11, 2022

(65) Prior Publication Data
US 2022/0265314 A1 Aug. 25, 2022

Related U.S. Application Data

(62) Division of application No. 17/139,806, filed on Dec. 31, 2020, now Pat. No. 11,357,543.

(51) Int. Cl.
*A61B 17/34* (2006.01)
*A61B 17/06* (2006.01)
*A61B 17/00* (2006.01)

(52) U.S. Cl.
CPC ..... *A61B 17/3423* (2013.01); *A61B 2017/00526* (2013.01)

(58) Field of Classification Search
CPC ............ A61B 17/3423; A61B 17/06; A61B 2017/00526; A61B 2017/00946; A61B 2017/00792; A61B 2017/06052
See application file for complete search history.

(56) References Cited

U.S. PATENT DOCUMENTS

| | | | | |
|---|---|---|---|---|
| 3,306,093 A * | 2/1967 | Sassak | ......... | B21D 5/0263 72/389.8 |
| 3,727,449 A * | 4/1973 | Johnston | ......... | B21D 7/04 72/389.8 |
| 4,967,585 A * | 11/1990 | Grimaldo | ......... | B21D 7/06 72/389.8 |
| 5,125,252 A * | 6/1992 | Ayres | ......... | B21D 7/02 72/157 |
| 6,523,388 B1 * | 2/2003 | Winton, III | ......... | B21D 7/066 72/389.8 |
| 7,624,612 B2 * | 12/2009 | Toda | ......... | B21D 7/04 72/389.8 |
| 9,486,851 B2 * | 11/2016 | Mizumura | ......... | B21D 7/06 |
| 10,507,310 B2 * | 12/2019 | Matlock | ......... | A61B 17/24 |
| 10,758,408 B1 * | 9/2020 | Passaglia | ......... | A61B 17/3421 |
| 11,267,214 B2 * | 3/2022 | Feistritzer | ......... | B23C 5/202 |
| 11,357,543 B1 * | 6/2022 | McCarthy | ......... | A61B 17/06 |
| 2006/0165828 A1 * | 7/2006 | Smilovici | ......... | B23C 5/202 425/352 |

(Continued)

OTHER PUBLICATIONS

Pristinewellnesscenter.com [online], "Thread-lift" Jul. 2020, [retrieved on Mar. 31, 2021], retrieved from: URL <https://www.pristinewellnesscenter.com/threadlift>, 7 pages.

*Primary Examiner* — Bayan Salone
(74) *Attorney, Agent, or Firm* — Fish & Richardson P.C.

(57) ABSTRACT

A cannula having multiple curves, devices for creating the cannula, and methods for using the cannula having multiple curves. One of the devices comprises two dies configured to mate together to transform a straight cannula into a double-curved cannula having two curves, and a base that is configured to slideably guide the two dies from respective initial positions to a mating position.

12 Claims, 9 Drawing Sheets

(56) References Cited

U.S. PATENT DOCUMENTS

| | | |
|---|---|---|
| 2016/0038338 A1* | 2/2016 | Rangel-Friedman .................. A61F 9/00781 606/107 |
| 2017/0246687 A1* | 8/2017 | Schwarz ................... F25D 3/08 |
| 2019/0232593 A1* | 8/2019 | Feistritzer ............... B23C 5/202 |
| 2022/0202445 A1 | 6/2022 | McCarthy et al. |

* cited by examiner

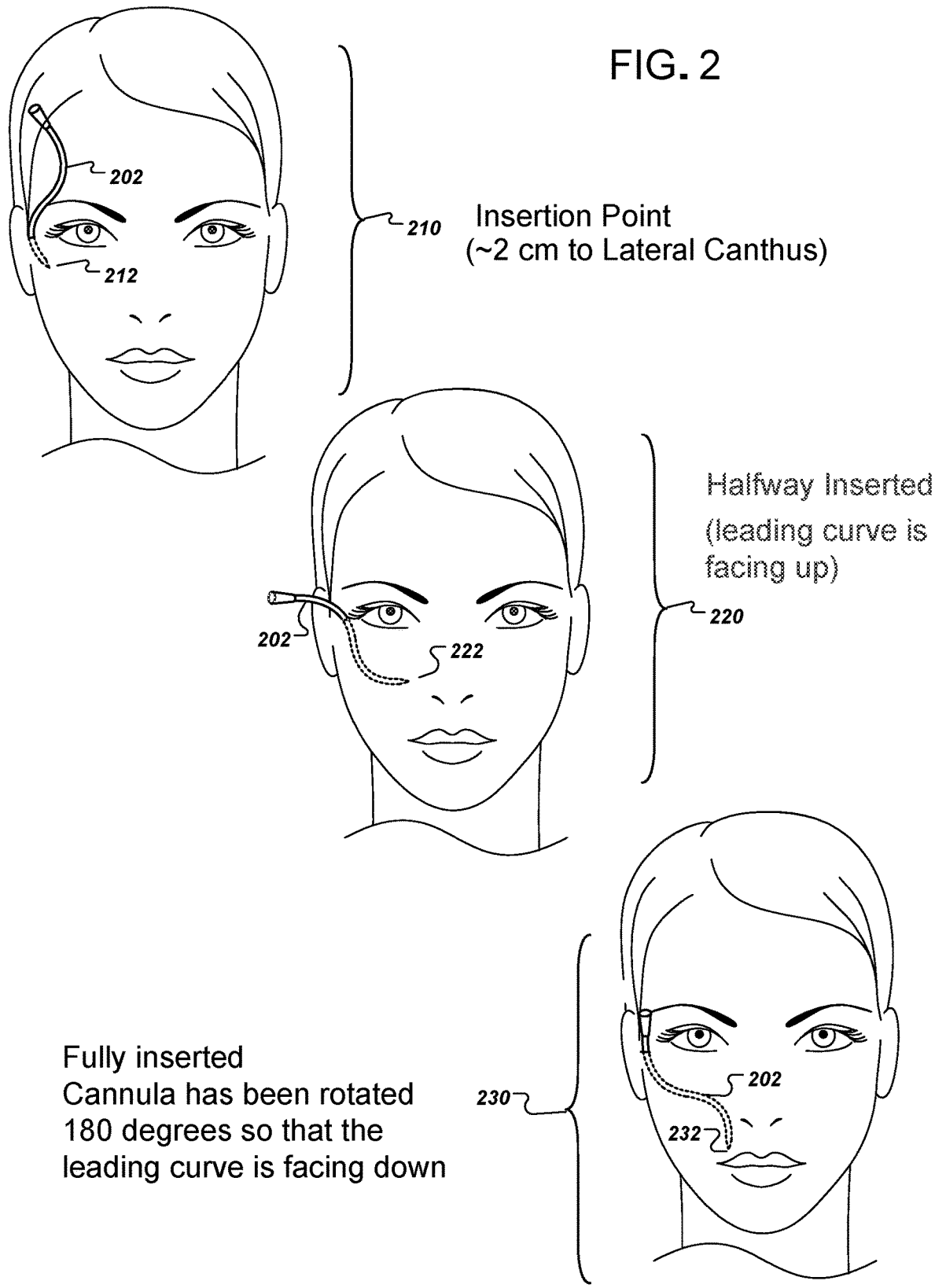

CURVED CANNULA

CLAIM OF PRIORITY

This application is a divisional application of, and claims priority to, U.S. patent application Ser. No. 17/139,806, filed on Dec. 31, 2020, entitled "CURVED CANNULA", which is herein incorporated by reference.

BACKGROUND

This specification relates to cannulas, and more particularly to cannulas for performing nonsurgical procedures including nonsurgical facelifts.

A cannula is a thin tube, typically made of metal, that can be inserted into the body. Cannulas can be used to perform nonsurgical percutaneous procedures, including facelifts. In this context, the term nonsurgical means a procedure that requires an incision that is substantially no larger than the width of the cannula itself. Therefore, using a cannula to perform a nonsurgical facelift is often referred to as a minimally invasive procedure, which typically does not require general anesthesia.

To perform a percutaneous facelift, a cannula equipped with a puncturing tip, e.g., a needle or a trocar, can be inserted through the skin of a patient's face. The cavity within the cannula can then be used to introduce hooked or barbed threads of an appropriate material, e.g., polydioxanone (PDO), into the cavity created by the cannula. These cavities created by a cannula may be referred to as thread paths. By applying tension to the threads introduced into the thread paths of the skin, the skin of the patient can be lifted or tightened.

Cannulas are generally manufactured to be as straight as possible. However, this straightness can introduce suboptimal results in nonsurgical procedures. In particular, a straight cannula tends to generate a thread path that is also straight, which can lead to suboptimal lifting results.

SUMMARY

This specification describes a double-curved cannula having multiple preformed curves, a technique for using the cannula, and a device for making double-curved cannulas.

Particular embodiments of the subject matter described in this specification can be implemented so as to realize one or more of the following advantages. Using a double-curved cannula for nonsurgical facelifts provides a superior lifting result because the curves of the cannula can make curved paths within the skin that follow the natural curves of the cheek. A single cannula can be used to introduce such curved paths, thereby providing superior results to using straight cannulas.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

FIG. 2 illustrates using a cannula having two preformed curves to perform a nonsurgical facelift.

Like reference numbers and designations in the various drawings indicate like elements.

DETAILED DESCRIPTION

Figure 1:
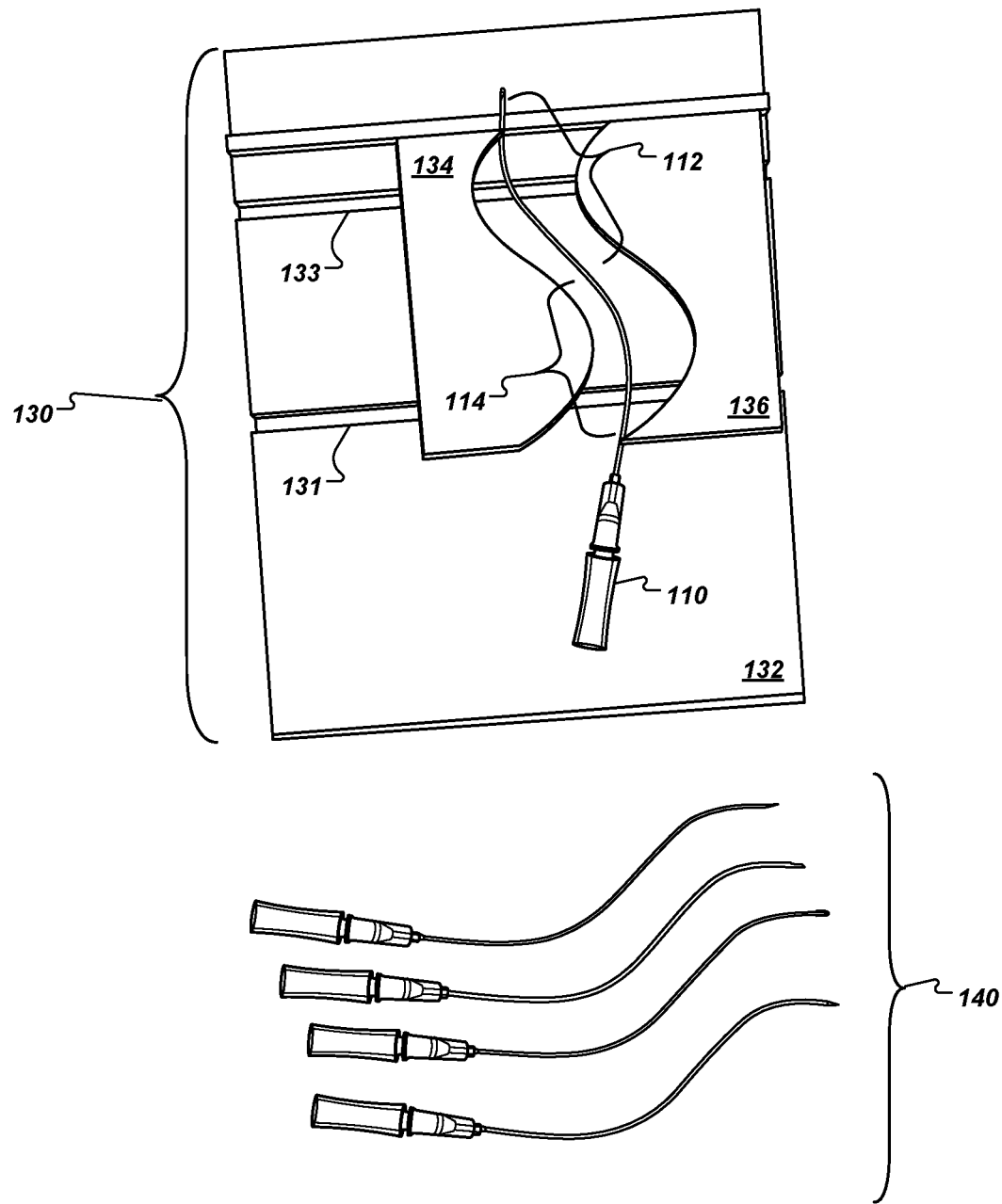
FIG. 1 is a diagram that illustrates a cannula having two preformed curves and a device for bending a straight cannula into a cannula having two preformed curves.

FIG. 1 is a diagram that illustrates a cannula having two preformed curves and a device for bending a straight cannula into a cannula having two preformed curves.

In this specification, a cannula having preformed curves means that the cannula has attained, before being used in a procedure on a patient, a stable shape exhibiting at least two curves that are observable to the naked eye. Typically, a cannula having two preformed curves will have one convex curve and one concave curve relative to a common reference frame.

The preformed curves can be introduced into the shape of a straight cannula at any appropriate time prior to a procedure being used on a patient. For example, a cannula can be manufactured to have two preformed curves. Alternatively or in addition, a cannula can be modified at one stage of a manufacturing process to have two preformed curves. As another example, a cannula can be bent by a doctor in a doctor's office just before the procedure is performed, e.g., using a device as described in this specification in more detail below. In this specification, a device used to introduce preformed curves in the shape of a cannula will be referred to as a jig.

An advantage to introducing the preformed curves at manufacturing time is that doctors performing the procedures need not re-sterilize the cannula before use, as is the case with bending the cannula with an on-site jig.

As shown in FIG. 1, the cannula 110 has two preformed curves 112 and 114. The curves 112 and 114 are oppositely convex and concave when observed from the same reference frame. The cannula 100 can have any appropriate gauge for performing the procedures described in this specification. For example, the cannula can be a 17-gauge, 18-gauge, 19-gauge, or 20-gauge cannula.

The cannulas can be any appropriate length for performing a particular percutaneous procedure. For example, the cannula can have a length that is appropriate based on the size of a patient's face or based on a representative size of a representative population of people.

As illustrated in FIG. 1, the curves 112 and 114 are substantially the same length and have substantially the same radius. However, the dimensions of the cannula can vary. For example, curves having differing lengths and radii can be used depending on the procedure being performed and on the preferences of the provider. In some implementations, each curve follows an arc for at least 20 degrees. In some other implementations, the curves are sinusoidal. Regardless of the exact shape, the preformed curves are generally noticeable from visual inspection, and the a cannula having two preformed curves as described is visually distinguishable from a straight cannula.

A jig 130 has two matable dies 134 and 136 and a base 132 that is configured to slideably guide the two matable dies from an initial position to a mated position. The sliding action is guided by two slots 131 and 133 in the base 132 that are configured to receive corresponding rails or tabs on the dies 134 and 136.

As can be observed from FIG. 1, due to elasticity of the cannula material, the curves of the jig 130 are typically more pronounced than the preformed curves that are imparted on the cannula 110. In other words, in order to achieve a particular desired curvature of the cannula 110, the jig 130 often has curves that are more pronounced or exaggerated relative to the desired curvature of the cannula 110.

The jig 130 can be operated by hand, e.g., by a doctor or another medical technician, or by machines, e.g., by one or more robots in a manufacturing facility.

As shown in FIG. 1, the jig 130 can be used to impart curves on cannulas having a variety of configurations 140 that may or may not be used for performing nonsurgical facelift procedures. In some implementations, the cannula 110 has a blunt, L-type tip.

FIG. 2 illustrates using a cannula 202 having two preformed curves to perform a nonsurgical facelift. In general, the cannula 202 has a leading curve and a trailing curve that arc in opposing directions. In some implementations, the curves are on substantially the same plane.

To perform the procedure, at step 1 210, the cannula 202 having two preformed curves is inserted at an insertion point 212 near the upper cheek. The insertion point 212 can be a predetermined distance from the lateral canthus, e.g., 1, 2, 3, or 4 cm from the lateral canthus. In FIG. 2, portions of the cannula that are underneath the skin are illustrated using dashed lines.

During a first portion of the insertion step, the leading curve of the cannula 202 follows a curved path from the insertion point 212 through the skin of the patient to a midway point 222 near the mid cheek. The leading curve of the cannula 202 thus maneuvers the cannula 202 around the cheekbone of the patient. As shown, at the midway point 222, the interior of the leading curve of the cannula 202 is facing up and to the inside of the patient's face.

After reaching the midway point 222, the cannula 202 is rotated while or before continuing the insertion process until reaching the end point 232. During this second portion of the insertion procedure, the leading point of the cannula 202 is inserted through the skin from the midway point 222 along a curved path to the end point 232.

During this process, the trailing curve of the cannula 202 substantially follows the curved path created by the leading curve of the cannula 202 during the first portion of the insertion step, e.g., the curved path from the insertion point 212 to the midway point 222.

The rotation maneuver can substantially rotate the cannula 202 between 90 and 270 degrees, e.g., substantially 180 degrees, about an axis passing between the leading curve and the trailing curve. When the tip of the cannula 202 reaches the end point 232, the rotation of the cannula 202 causes the interior of the leading curve of the cannula 202 to be facing down and to the outside of the patient's face.

This procedure can cause the leading curve of the cannula 202 to follow the ogee curve of the patient's face. In this specification, an ogee curve is a curve defined by the malar or cheekbone prominence. Thus, the cannula 202 can be bent to have a preformed leading curve defined by a representative ogee curve. The shape of the representative ogee curve can be defined with respect to a population of patients or a measure of central tendency of a population of patients.

After reaching the end point, the cannula 202 can be removed by reversing the order of steps. Upon initiating the removal process, barbs on threads within the cannula 202 can latch onto skin within the curved paths created by the cannula 202, thereby leaving a thread within the skin along the curved path created by the cannula 202. Applying tension to the thread left along the curved path created by the cannula 202 can provide a superior lifting result to prior art techniques. In particular, the lifting direction of the skin follows the contours of the patient's face, thereby providing a more natural-looking result.

Typically, the procedure illustrated in FIG. 2 is repeated multiple times to introduce threads along multiple curved paths.

Figure 3A:
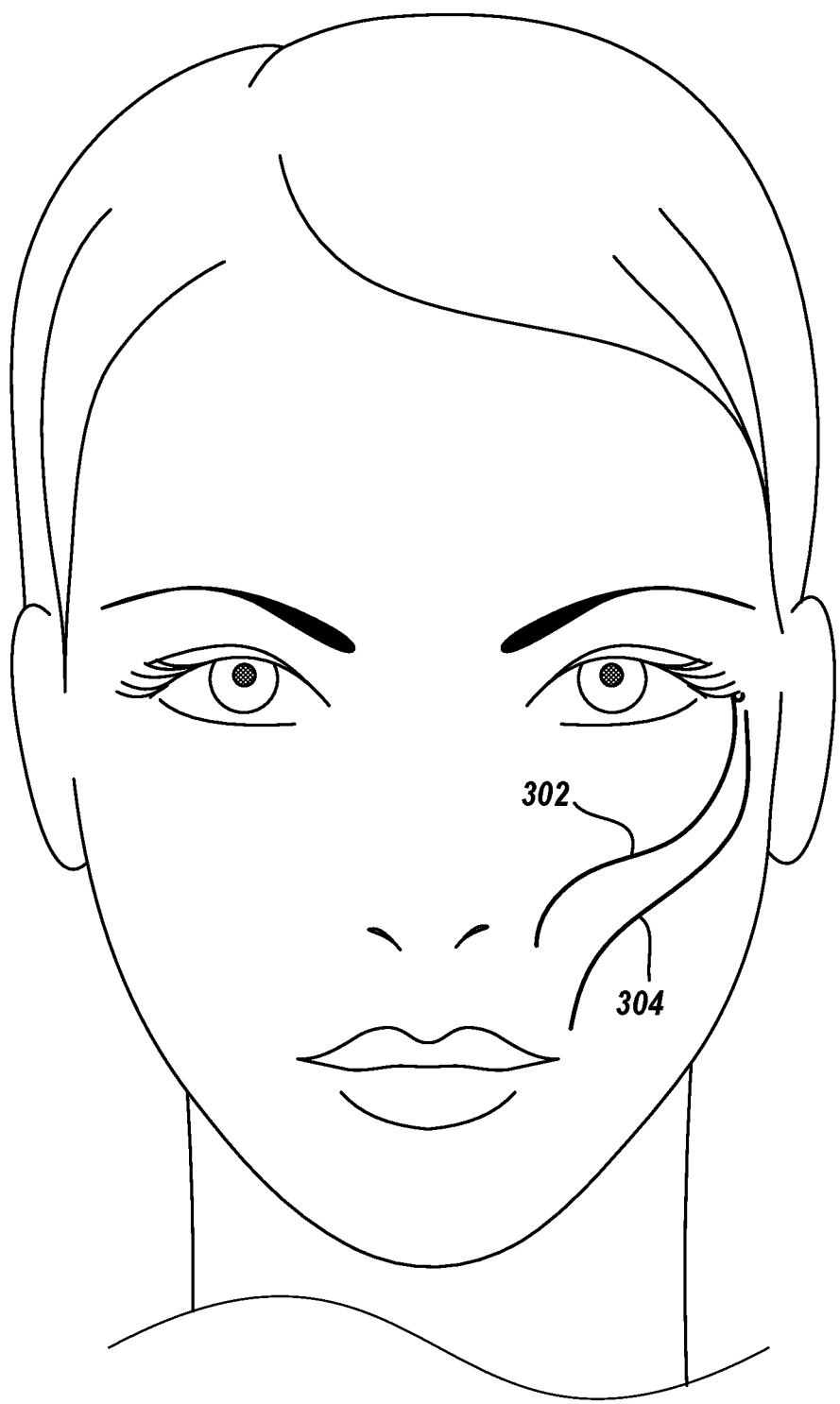
FIG. 3A illustrates example paths that follow the ogee curve of a patient's face.

FIG. 3A illustrates example paths 302, 304 that follow the ogee curve of a patient's face.

Figure 3B:
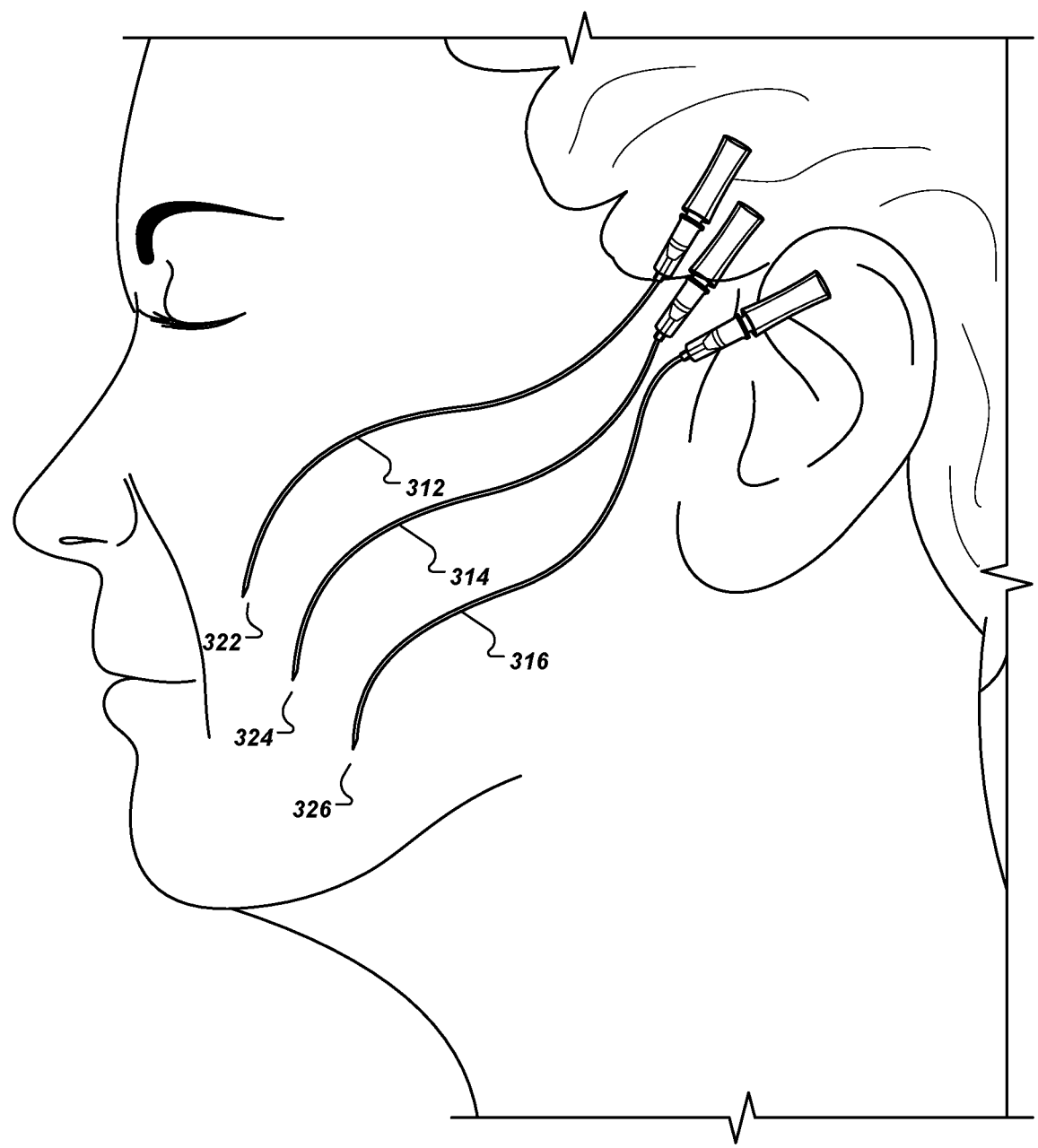
FIG. 3B illustrates additional examples of curved paths that can be created by an insertion process that involves rotating a double-curved cannula.

FIG. 3B illustrates additional examples of curved paths that can be created by an insertion process that involves rotating a double-curved cannula. As shown, the curved paths 312, 314, and 316 follow the contour of the patient's face from an insertion point to respective end points 322, 324, and 326.

Applying tension to the threads left within the curved paths 312, 314, and 216 has the effect of lifting the skin of the face along the contours of the face, thereby providing a more natural lift than prior art techniques that use straight cannulas.

Figure 4:
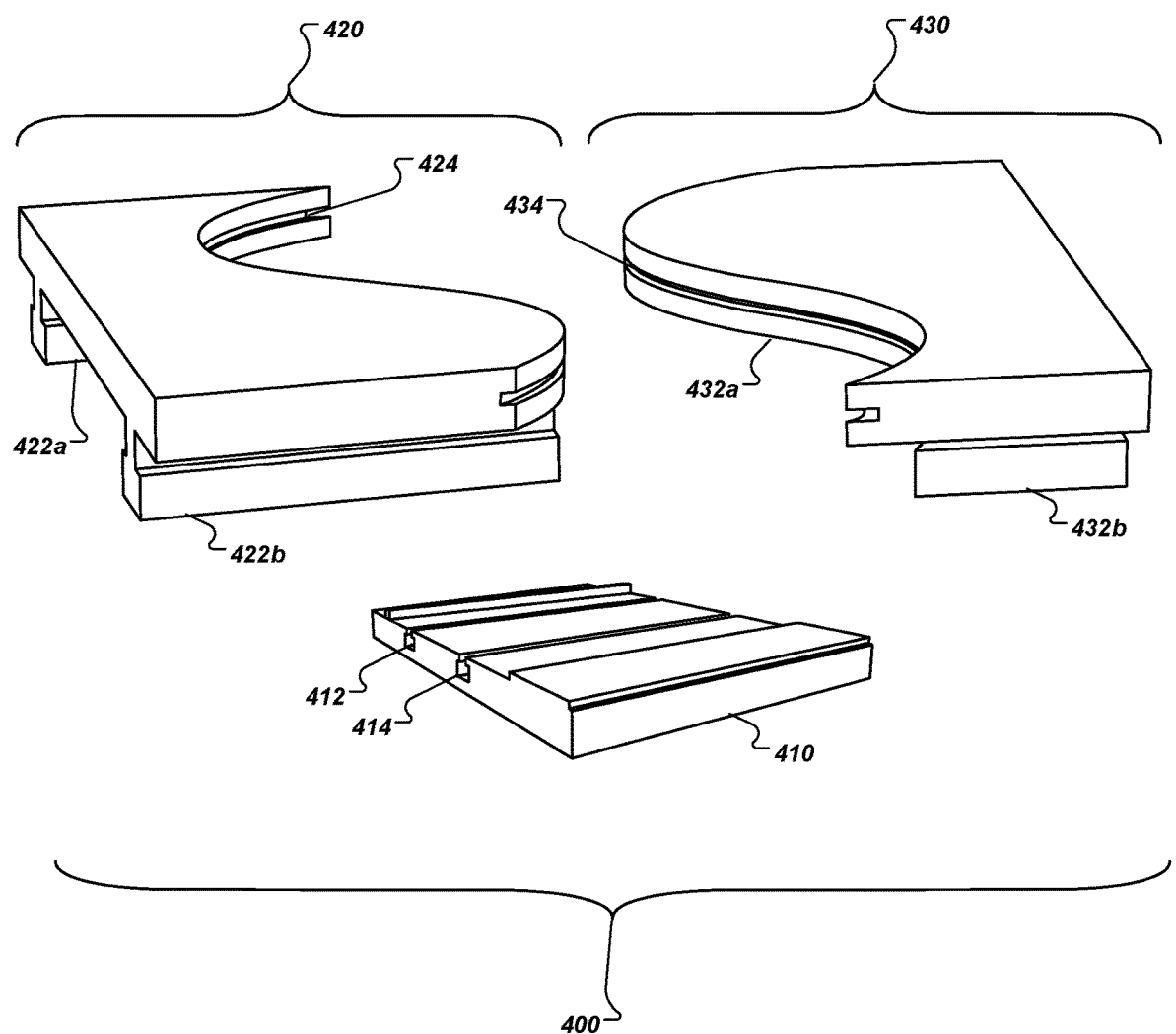
FIG. 4 illustrates an exploded view of an example jig having a base and two matable dies.

FIG. 4 illustrates an exploded view of an example jig 400 having a base 410 and two matable dies 420 and 430. The example jig is an example of a mechanism that can reliably bend cannulas into a same shape over and over.

As shown, the base 410 has two slots 412, 414 that are configured to receive corresponding rails 422*a-b* and 432*a-b* of respective dies 420 and 430. (From this perspective, the rail 432*a* is indicated but not visible). The base 410 can have any appropriate mechanism for consistently guiding the dies 420, 430 to a mating position. For example, the base 410 can have tabs that correspond to the slots 412, 414.

Each die 420 and 430 has one or more rails 422*a-b* or 432*a-b* that are configured to slide along the slots 412, 414 in the base 410. In the example illustrated in FIG. 4, the rails 432*a-b* and 432*a-b* are T-shaped to be compatible with T-shaped slots 412, 414 in the base 410, which reduces perpendicular motion when mating the dies 420, 430.

Each die 420 and 430 is fashioned with a curved surface that defines one or more curves. The curves of the dies 420 and 430 together are mirrored so that they fit together during the mating process. As described above, a cannula can be bent to have a leading curve defined by a representative curve, e.g., an ogee curve. Because of the pliability of metal materials, obtaining an appropriate representative curve in the cannula can require the dies 420 and 430 to have an exaggerated or more pronounced or severe curve than the desired representative curve.

Each die 420 and 430 also has a groove 424 and 434 to receive a cannula and hold the cannula in place during the bending process. Each die 420 and 430 can alternatively or in addition have any other appropriate mechanism for holding a cannula in place during the mating process, e.g., ridges or fastening components.

After placing a cannula into the jig 400, the two dies 420 and 430 having curves that mirror each other are closed or otherwise pressed together. The action of closing together the two dies 420 and 430 causes the metal cannula to be bent into a precise and reproducible shape. In some cases, the dies 420 and 430 are held together for several seconds in order to set the curved shape of the metal cannula.

The closing action of the jig 400 can be performed by a machine or by hand. For example, the jig 400 can be a part of an assembly line system in a factory. Assembly machines or robots can output straight cannulas. The cannulas can then be bent by a jig into curved cannulas. The curved cannulas can then be sterilized and packaged for distribution.

Alternatively, the example jig 400 can be used to bend a straight cannula after manufacturing and distribution. For example, a doctor can use the jig 400 in a clinic setting to transform a straight cannula into a curved cannula. Typically, this process would involve resterilizing the cannula after it is bent into shape.

FIGS. 5A-D illustrate hand operation of an example jig.

Figure 5A:
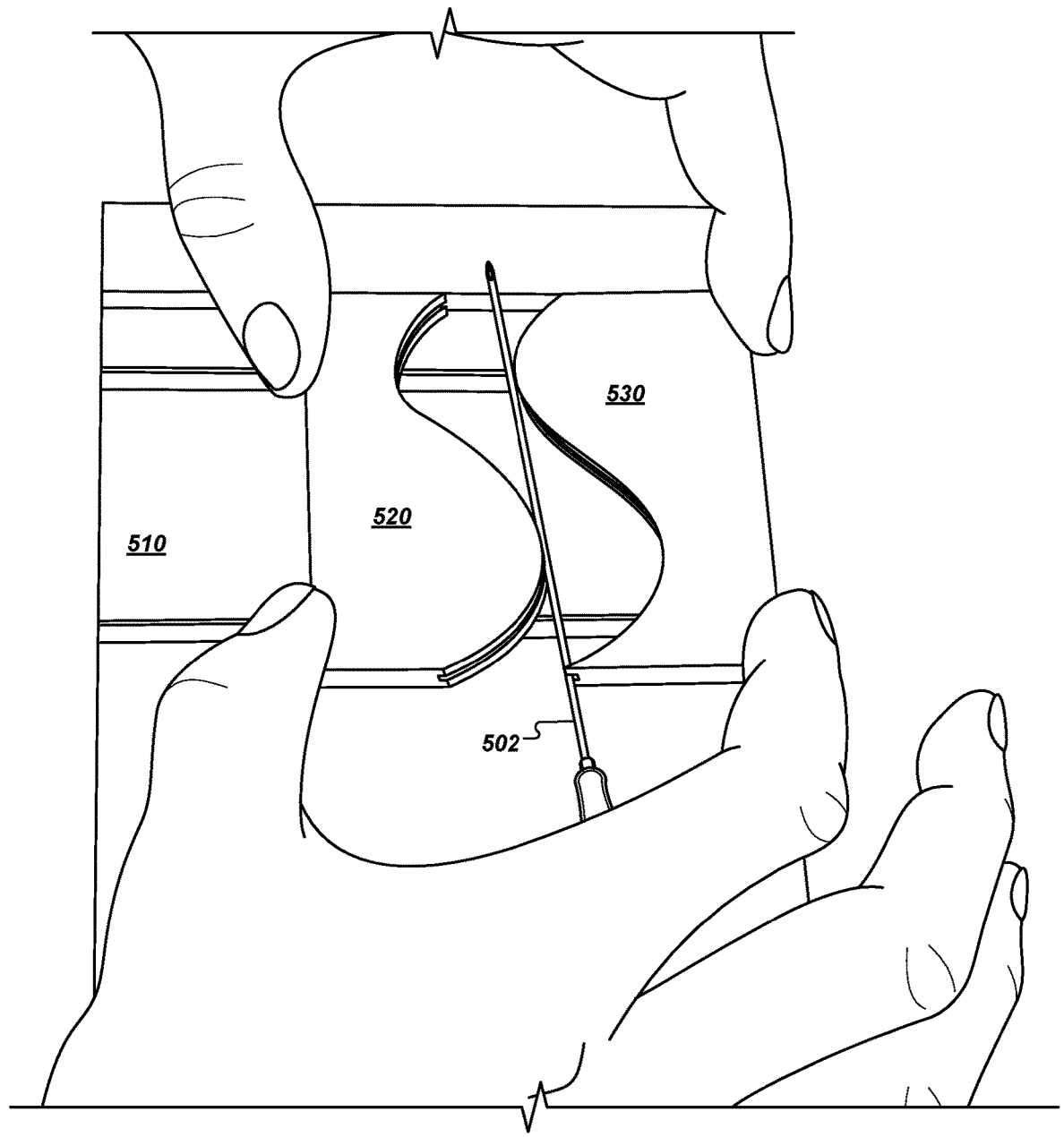
FIGS. 5A-D illustrate hand operation of an example jig.

As shown in FIG. 5A, a straight cannula 502 is placed so that it is resting on the base 510 of the jig. The bending process starts by engaging the straight cannula with the grooves on the dies 520 and 530. Engaging with the grooves on the dies 520 and 530 holds the cannula in place during the bending process.

Figure 5B:
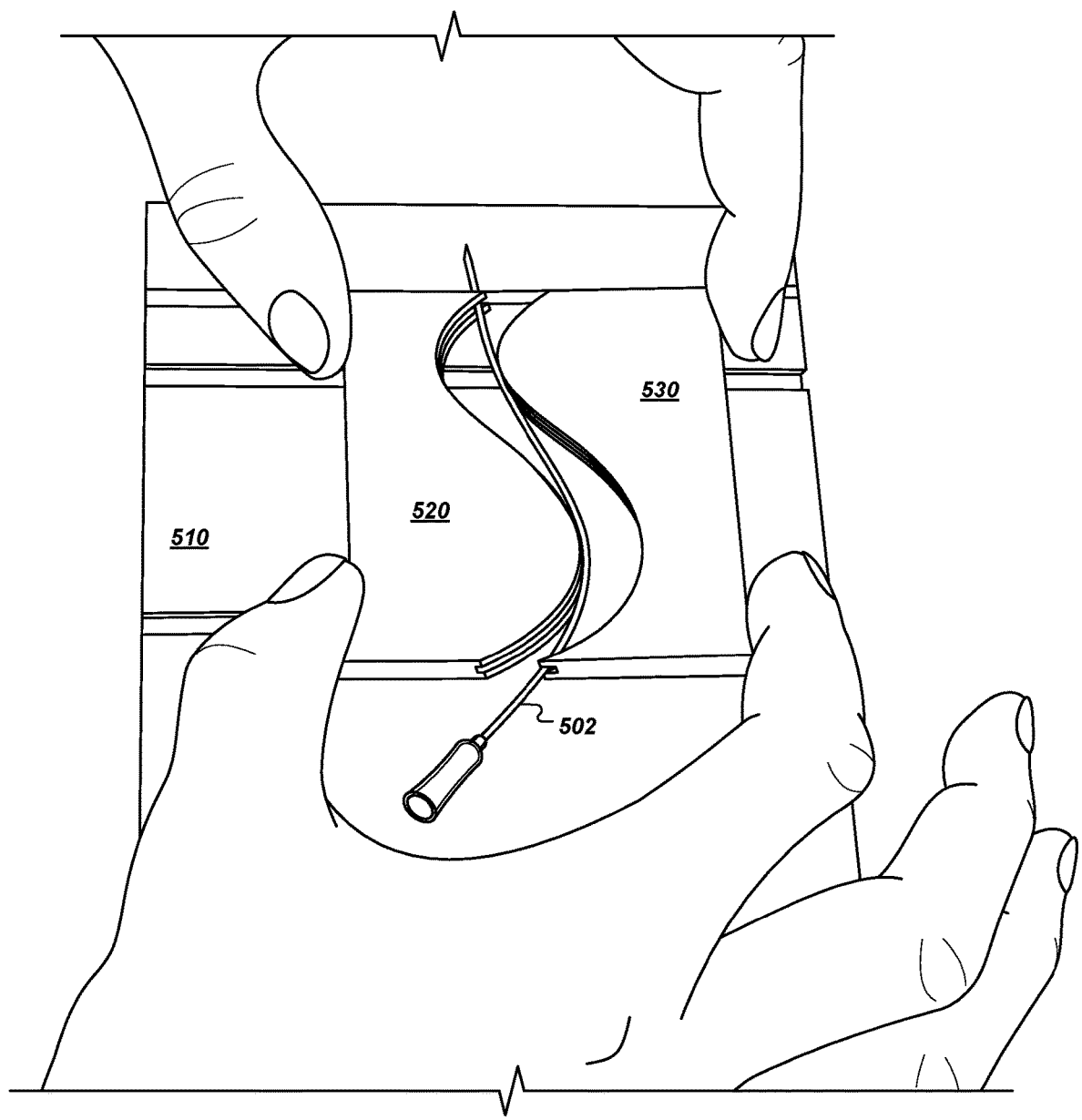
Figure 5C:
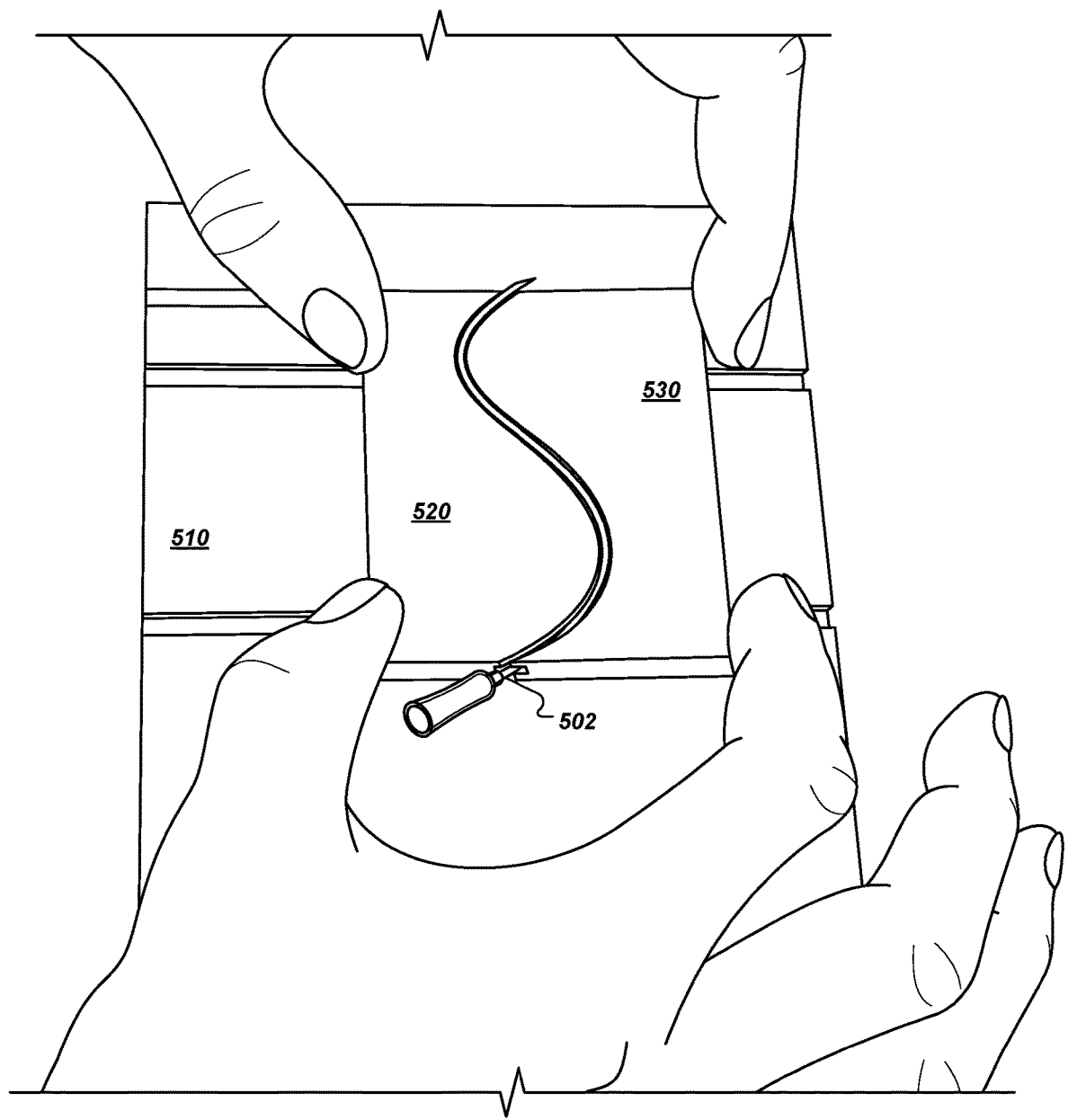

The dies 520 and 530 are then pressed together into a mating position as shown in the sequence illustrated in FIGS. 5B and 5C. As illustrated, this process can be performed by hand. Alternatively, the process can be performed by industrial machines in an assembly line or by one or more robots. In some cases, the fully mated position is held for a duration lasting between 1 and 5 seconds in order to fully bend the cannula 502.

Figure 5D:
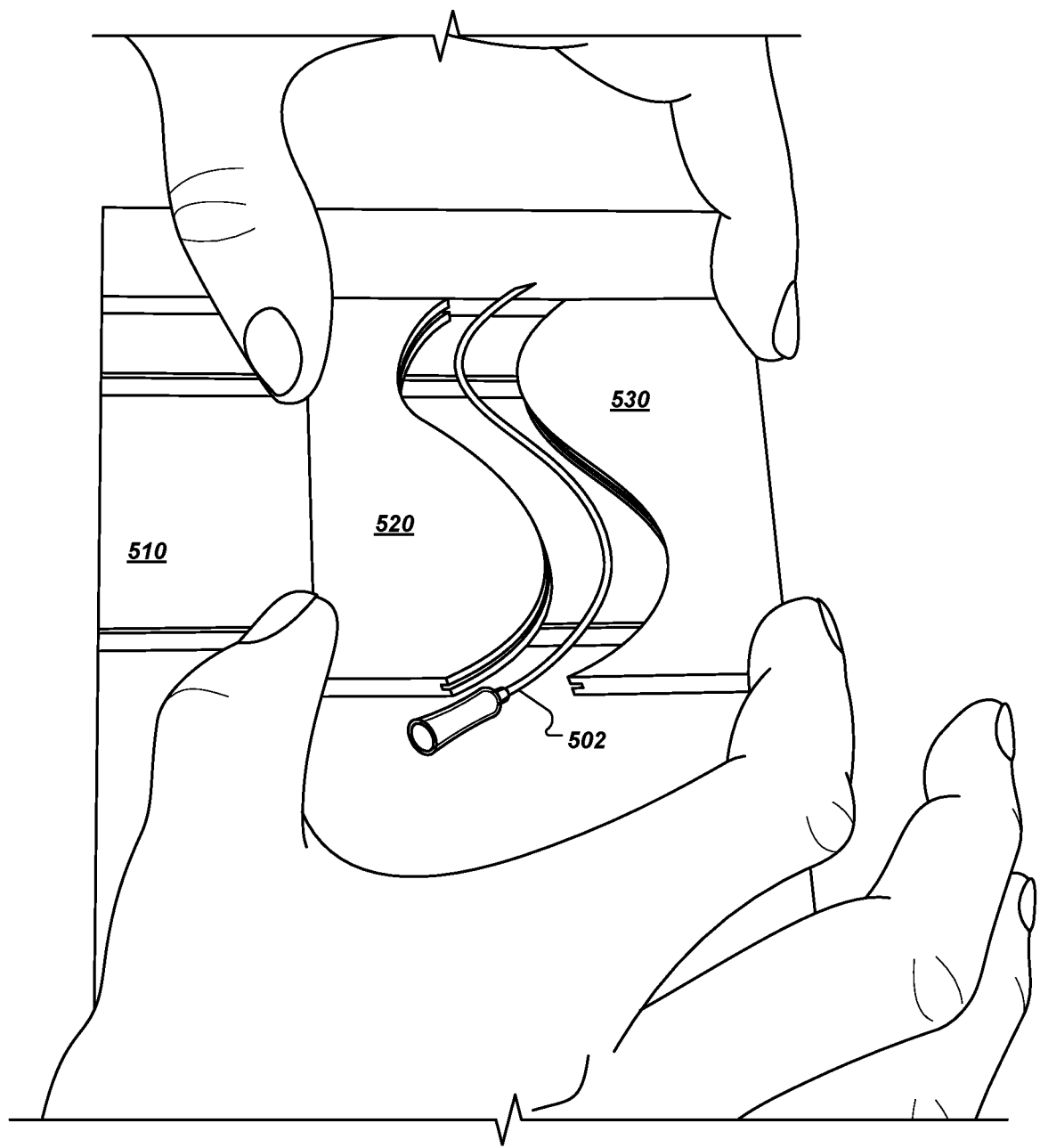

As shown in FIG. 5D, the dies are opened. In some implementations, the base is spring-loaded so that the rails of the dies 520 and 530 are forced open when a user or a machine no longer applies inward force to the dies 520 and 530.

As illustrated in FIG. 5D, the previously straight cannula now has two noticeable curves imparted by the dies 520 and 530, which remain in the cannula after the dies 520 and 530 are opened. Because of the properties of the metal used in the cannula, the curves of the bent cannula are typically less pronounced than the curves of the dies 520 and 530. Therefore, the dies 520 and 530 can be manufactured to have more pronounced curves that result in a cannula having curves to match a particular representative curve, e.g., a representative ogee curve.

In addition to the embodiments described above, the following embodiments are also innovative:

Embodiment 1 is a cannula having two preformed curves.

Embodiment 2 is the cannula of embodiment 1, wherein each of the preformed curves follows a respective arc for at least 20 degrees.

Embodiment 3 is the cannula of any one of embodiments 1-3, wherein the two preformed curves are sinusoidal.

Embodiment 4 is the cannula of any one of embodiments 1-3, wherein the two preformed curves are convex and concave respectively.

Embodiment 5 is the cannula of any one of embodiments 1-4, wherein the two preformed curves comprise a leading curve and a trailing curve.

Embodiment 6 is the cannula of embodiment 5, wherein the leading curve is defined by a representative ogee curve.

Embodiment 7 is the cannula of embodiment 6, wherein the representative ogee curve is defined from a population of patients.

Embodiment 8 is a jig comprising:
two dies configured to mate together to transform a straight cannula into a double-curved cannula having two curves; and
a base that is configured to slideably guide the two dies from respective initial positions to a mating position.

Embodiment 9 is the jig of embodiment 8, wherein one or more of the dies comprises a groove configured to receive the straight cannula.

Embodiment 10 is the jig of any one of embodiments 8-9, wherein the base has one or more slots configured to guide the two dies from the respective initial positions to a mating position.

Embodiment 11 is the jig of embodiment 10, wherein the dies comprise rails or tabs that are guided by the one or more slots of the base.

Embodiment 12 is the jig of any one of embodiments 8-10, wherein one or more of the dies have a curve that is defined by a representative ogee curve.

Embodiment 13 is the jig of embodiment 12, wherein the curves of the dies are more pronounced than the representative ogee curve such that the dies impart a curve on a cannula having the representative ogee curve.

Embodiment 14 is the jig of embodiment 12, wherein the representative ogee curve is defined from a population of patients.

Embodiment 15 is a method of forming a double-curved cannula having two curves comprising:
placing a straight cannula in a jig having two matable dies; and
moving the matable dies together into a mating position, thereby forming the double-curved cannula.

Embodiment 16 is the method of embodiment 15, wherein placing the straight cannula in the jig comprises resting the cannula on a base of the jig.

Embodiment 17 is the method of embodiment 16, further comprising engaging the straight cannula with a groove on one of the matable ties.

Embodiment 18 is the method of any one of embodiments 15-17, wherein the dies have a curve that is defined by a representative ogee curve.

Embodiment 19 is the method of embodiment 18, wherein the curve of the dies is more pronounced than the representative ogee curve such that the dies impart the representative curve on the cannula when the dies are opened.

Embodiment 20 is the method of embodiment 18, wherein the representative ogee curve is defined from a population of patients.

Embodiment 21 is the method of any one of embodiments 15-20, wherein moving the dies together is performed by a machine on an assembly line or by one or more robots.

Embodiment 22 is the method of any one of embodiments 15-20, wherein moving the dies together is performed manually.

Embodiment 23 is a method comprising performing a nonsurgical facelift using a cannula having two preformed curves.

Embodiment 24 is the method of embodiment 23, wherein using the cannula having two preformed curves comprises:
initially inserting the cannula at an initial insertion point near an upper cheek of a patient;
inserting a leading curve of the cannula along a curved path from the insertion point to a midway point;
rotating the cannula; and
inserting a trailing curve of the cannula.

Embodiment 25 is the method of embodiment 24, wherein rotating the cannula comprises rotating the cannula between 90 and 270 degrees.

Embodiment 26 is the method of any one of embodiments 24-25, wherein rotating the cannula causes an orientation of an interior of the leading curve of the cannula to face down and to an outside of a patient's face.

Embodiment 27 is the method of embodiment 26, wherein before rotating the cannula, the orientation of the interior of the leading curve of the cannula faces up and to the inside of the patient's face.

Embodiment 28 is the method of any one of embodiments 24-27, further comprising:
 removing the cannula along the curved path; and
 applying tension to a thread left by the cannula along the curved path to effectuate the nonsurgical facelift.

Embodiment 29 is the method of any one of embodiments 24-28, wherein the curved path follows an ogee curve of the patient's face.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system modules and components in the embodiments described above should not be understood as requiring such separation in all embodiments.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results.

What is claimed is:

1. A cannula having two preformed curves, wherein the two preformed curves comprise a leading curve and a trailing curve, and wherein the leading curve is defined by a representative ogee curve.

2. The cannula of claim 1, wherein each of the preformed curves is at least 20 degrees.

3. The cannula of claim 1, wherein the two preformed curves are sinusoidal.

4. The cannula of claim 1, wherein the two preformed curves are convex and concave respectively.

5. The cannula of claim 1, wherein the representative ogee curve is defined from a population of patients.

6. A method comprising performing a nonsurgical facelift using a cannula having two preformed curves.

7. The method of claim 6, wherein using the cannula having two preformed curves comprises:
 initially inserting the cannula at an initial insertion point near an upper cheek of a patient;
 inserting a leading curve of the cannula along a curved path from the initial insertion point to a midway point;
 rotating the cannula; and
 inserting a trailing curve of the cannula.

8. The method of claim 7, wherein rotating the cannula comprises rotating the cannula between 90 and 270 degrees.

9. The method of claim 7, wherein rotating the cannula causes an orientation of an interior of the leading curve of the cannula to face down and to an outside of a patient's face.

10. The method of claim 9, wherein before rotating the cannula, the orientation of the interior of the leading curve of the cannula faces up and to the inside of the patient's face.

11. The method of claim 7, further comprising:
 removing the cannula along the curved path; and
 applying tension to a thread left by the cannula along the curved path to effectuate the nonsurgical facelift.

12. The method of claim 7, wherein the curved path follows an ogee curve of the patient's face.

* * * * *